(12) United States Patent
Schafer et al.

(10) Patent No.: US 11,373,330 B2
(45) Date of Patent: Jun. 28, 2022

(54) IMAGE-BASED GUIDANCE FOR DEVICE PATH PLANNING BASED ON PENALTY FUNCTION VALUES AND DISTANCES BETWEEN ROI CENTERLINE AND BACKPROJECTED INSTRUMENT CENTERLINE

(71) Applicants: Siemens Medical Solutions USA, Inc., Malvern, PA (US); Siemens Healthcare GmbH, Erlangen (DE)

(72) Inventors: Sebastian Schafer, Madison, WI (US); Randolph M. Setser, Cornelius, NC (US); Maddalena Strumia, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 274 days.

(21) Appl. No.: 15/936,491

(22) Filed: Mar. 27, 2018

(65) Prior Publication Data
US 2019/0304129 A1    Oct. 3, 2019

(51) Int. Cl.
*G06T 7/73* (2017.01)
*A61B 1/267* (2006.01)
(Continued)

(52) U.S. Cl.
CPC .............. *G06T 7/74* (2017.01); *A61B 1/2676* (2013.01); *A61B 34/20* (2016.02); *A61B 34/25* (2016.02);
(Continued)

(58) Field of Classification Search
CPC ... G06T 7/74; G06T 7/11; G06T 7/174; G06T 11/006; G06T 2207/10028;
(Continued)

(56) References Cited

U.S. PATENT DOCUMENTS 7,167,180 B1 *   1/2007   Shibolet .................... G06T 7/13
                                                         345/474
7,574,024 B2 *   8/2009   Bitter ...................... G06T 15/10
                                                         382/128
(Continued)

FOREIGN PATENT DOCUMENTS

CN        1602166 A       3/2005
CN        1681448 A      10/2005
(Continued)

OTHER PUBLICATIONS

Reynisson, Pall J., et al. "Navigated bronchoscopy: a technical review." Journal of bronchology & interventional pulmonology 21.3 (2014): 242-264. (Year: 2014).*
(Continued)

*Primary Examiner* — Serkan Akar
*Assistant Examiner* — Richmond J Van Winter

(57) ABSTRACT

Systems and methods for image-based guidance for facilitating navigation of tubular networks. A region of interest in three-dimensional image data may first be segmented. An endoscopic instrument may be detected in two-dimensional intraoperative image data of the region of interest. A centerline of the detected endoscopic instrument may then be determined. The endoscopic instrument and the centerline may be backprojected to generate a three-dimensional backprojected volume. A device path of the endoscopic instrument may be generated based at least in part on the three-dimensional backprojected volume and the three-dimensional image data.

12 Claims, 9 Drawing Sheets

(51) Int. Cl.
*A61B 34/20* (2016.01)
*A61B 34/00* (2016.01)
*G06T 7/11* (2017.01)
*G06T 7/174* (2017.01)
*G06T 11/00* (2006.01)
*A61B 5/055* (2006.01)
*A61B 5/06* (2006.01)
*A61B 1/00* (2006.01)

(52) U.S. Cl.
CPC .......... *G06T 7/11* (2017.01); *G06T 7/174* (2017.01); *G06T 11/006* (2013.01); *A61B 2034/2057* (2016.02); *A61B 2034/2065* (2016.02); *G06T 2207/10028* (2013.01); *G06T 2207/10064* (2013.01); *G06T 2207/10068* (2013.01); *G06T 2207/10081* (2013.01); *G06T 2207/10088* (2013.01); *G06T 2207/30021* (2013.01); *G06T 2207/30061* (2013.01); *G06T 2207/30172* (2013.01)

(58) Field of Classification Search
CPC . G06T 2207/10064; G06T 2207/10081; G06T 2207/10088; G06T 2207/10068; G06T 2207/30021; G06T 2207/30061; G06T 2207/30172; G06T 11/008; G06T 2207/10121; G06T 2207/10016; G06T 2207/10072; G06T 2211/421; A61B 34/20; A61B 34/25; A61B 1/2676; A61B 2034/2065; A61B 2034/2057; A61B 5/055; A61B 2034/2051; A61B 5/066; A61B 5/062; A61B 1/00009
See application file for complete search history.

(56) References Cited

U.S. PATENT DOCUMENTS

| | | | | |
|---|---|---|---|---|
| 2005/0096589 | A1* | 5/2005 | Shachar | A61B 1/00158 604/95.01 |
| 2008/0097155 | A1* | 4/2008 | Gattani | A61B 34/20 600/117 |
| 2008/0183073 | A1* | 7/2008 | Higgins | A61B 6/469 600/425 |
| 2012/0059248 | A1* | 3/2012 | Holsing | A61B 5/062 600/424 |
| 2015/0282890 | A1* | 10/2015 | Cohen | A61B 5/7289 600/424 |
| 2016/0374562 | A1* | 12/2016 | Vertikov | A61B 1/0005 600/424 |
| 2018/0116722 | A1* | 5/2018 | Koyrakh | A61B 34/20 |
| 2019/0076102 | A1* | 3/2019 | Mistretta | A61B 6/4057 |

FOREIGN PATENT DOCUMENTS

| | | |
|---|---|---|
| CN | 1722981 A | 1/2006 |
| CN | 1836255 A | 9/2006 |
| CN | 1891153 A | 1/2007 |
| CN | 1936958 A | 3/2007 |
| CN | 101433464 A | 5/2009 |
| CN | 101442934 A | 5/2009 |
| CN | 101809618 A | 8/2010 |
| CN | 101836235 A | 9/2010 |
| CN | 101849842 A | 10/2010 |
| CN | 103026252 A | 4/2013 |
| CN | 104188725 A | 12/2014 |
| CN | 106999246 A | 8/2017 |
| DE | 102006002907 A1 | 7/2007 |
| JP | 2010509976 A | 4/2010 |

OTHER PUBLICATIONS

M. W. Jones, J. A. Baerentzen and M. Sramek, "3D distance fields: a survey of techniques and applications," in IEEE Transactions on Visualization and Computer Graphics, vol. 12, No. 4, pp. 581-599, Jul.-Aug. 2006, doi: 10.1109/TVCG.2006.56. (Year: 2006).*

Schafer, Sebastian et al. "Evaluation of guidewire path reproducibility." Medical physics vol. 35,5 (2008): 1884-92. doi: 10.1118/1.2903430 (Year: 2008).*

Reynisson, Pall J., et al. "Navigated bronchoscopy: a technical review." Journal of bronchology & interventional pulmonology 21.3 (2014): 242-264.

Hohenforst-Schmidt, Wolfgang, et al. "Radiation exposure of patients by cone beam CT during endobronchial navigation-a phantom study." Journal of Cancer 5.3 (2014): 192.

* cited by examiner

IMAGE-BASED GUIDANCE FOR DEVICE PATH PLANNING BASED ON PENALTY FUNCTION VALUES AND DISTANCES BETWEEN ROI CENTERLINE AND BACKPROJECTED INSTRUMENT CENTERLINE

TECHNICAL FIELD

The present disclosure generally relates to image data processing, and more particularly to image-based guidance for navigating tubular networks.

BACKGROUND

Lung cancer is a frequent and deadly disease. Early, precise, fast and cost-effective diagnosis and treatment of lung lesions are important to enhance survival rates for patients. To perform diagnosis and therapy, clinicians typically use bronchoscopy to visualize the inside of airways. Bronchoscopy involves the use of a bronchoscope to examine the airways of a patient for abnormalities (e.g., bleeding, tumors, lesions, foreign bodies, inflammation). The bronchoscope is usually inserted into a patient's airway through the patient's nose or mouth and can extend into the lungs of the patient.

Bronchoscopes, however, are limited in how far they may be advanced through the airway due to their size before becoming wedged in the airway of the patient. Where the bronchoscope is too large to reach a target location deep in the lungs (e.g., beyond third-fourth generation of branching of airways), a clinician may utilize certain real-time imaging modalities to initially determine the location of a target tissue and to confirm the location of the target tissue. If the clinician is unable to reach the target tissue for any reason, the clinician may insert a navigated percutaneous catheter to the confirmed location of the target tissue.

Traditional navigation techniques, however, have downfalls, such as outdated imaging data, deformation of the airway that is not accounted for and difficulty of use even for advanced users. Reliable and accurate guidance is important for success in biopsy and treatment procedures in bronchoscopy.

SUMMARY

Described herein are systems and methods for image-based guidance for facilitating navigation of tubular networks. A region of interest in three-dimensional image data may first be segmented. An endoscopic instrument may be detected in two-dimensional intraoperative image data of the region of interest. A centerline of the detected endoscopic instrument may then be determined. The endoscopic instrument and the centerline may be backprojected to generate a three-dimensional backprojected volume. A device path of the endoscopic instrument may be generated based at least in part on the three-dimensional backprojected volume and the three-dimensional image data.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
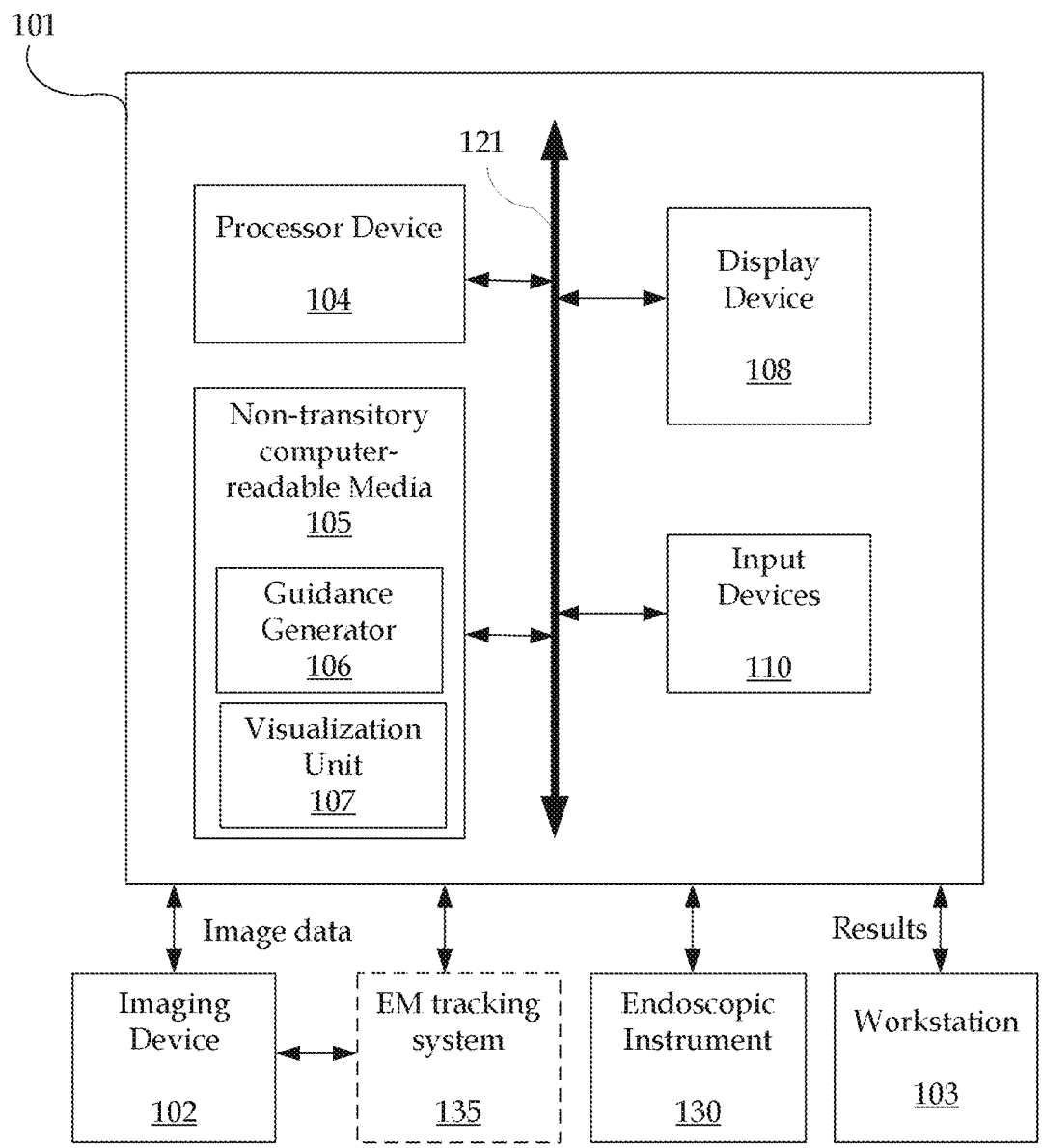
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images, voxels for 3D images, dynamic voxels or doxels for 4D datasets). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture, 3D volume or 4D dataset. For a 2- or 3-Dimensional image, the domain of the image is typically a 2- or 3-Dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, "voxels" for volume image elements, often used with respect to 3D imaging, and "doxels" for 4D datasets can be used interchangeably. It should be noted that the 3D volume image is itself synthesized from image data obtained as pixels on a 2D sensor array and displays as a 2D image from some angle of view. Thus, 2D image processing and image analysis techniques can be applied to the 3D volume image data. In the description that follows, techniques described as operating upon doxels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel", "subject voxel" and "subject doxel" are used to indicate a particular image element as it is operated upon using techniques described herein.

One aspect of the present framework facilitates guidance through a tubular network via the use of image data. A tubular network generally refers to a luminal branched structure, such as a bronchial or lung network, in which an endoscopic instrument (e.g., bronchoscope) may be inserted. The image data is acquired using an imaging technique, such as fluoroscopy. A guidance solution based on information obtained from the image data alone advantageously enhances the workflow and positioning of fixed or mobile C-arms for image acquisition.

Another aspect of the present framework facilitates guidance through tubular networks via the use of image data and electromagnetic (EM) guidance. Traditional EM tracking techniques do not consider fluoroscopic or other image-based information to accurately depict the position of the endoscopic instrument. Combining both information sources advantageously yields improved accuracy. These and other exemplary features and advantages will be described in more details herein.

It is understood that while a particular application directed to transbronchial network navigation may be shown, the technology is not limited to the specific implementations illustrated. For example, the technology may be applied to other types of tubular networks, such as the gastrointestinal tract, the ear, the urinary tract and so forth.

FIG. 1 is a block diagram illustrating an exemplary system 100. The system 100 includes a computer system 101 for implementing the framework as described herein. Computer system 101 may be a desktop personal computer, a portable laptop computer, another portable device, a mini-computer, a mainframe computer, a server, a cloud infrastructure, a storage system, a dedicated digital appliance, a communication device, or another device having a storage sub-system configured to store a collection of digital data items. In some implementations, computer system 101 operates as a standalone device. In other implementations, computer system 101 may be connected (e.g., using a network) to other machines, such as imaging device 102, workstation 103, endoscopic instrument 130 and optional electromagnetic (EM) tracking system 135. In a networked deployment, computer system 101 may operate in the capacity of a server (e.g., thin-client server, such as syngo®.via by Siemens Healthcare), a client user machine in server-client user network environment, or as a peer machine in a peer-to-peer (or distributed) network environment.

Computer system 101 may include a processor device or central processing unit (CPU) 104 coupled to one or more non-transitory computer-readable media 105 (e.g., computer storage or memory), display device 108 (e.g., monitor) and various input devices 110 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in one or more non-transitory computer-readable media 105. In particular, the present techniques may be implemented by a guidance generator 106 and a visualization unit 107. One or more non-transitory computer-readable media 105 may include random access memory (RAM), read-only memory (ROM), magnetic floppy disk, flash memory, and other types of memories, or a combination thereof. The computer-readable program code is executed by processor device 104 to process data, images or image data acquired by, for example, imaging device 102, endoscopic instrument 130 and EM tracking system 135. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing image datasets, a knowledge base and so forth. Such data may also be stored in external storage or other memories. The external storage may be implemented using a database management system (DBMS) managed by the processor device 104 and residing on a memory, such as a hard disk, RANI, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The imaging device 102 may be a radiology scanner, such as an C-arm fluoroscopic X-ray or CT scanner, for acquiring image data. The workstation 103 may include a computer and appropriate peripherals, such as a keyboard and display device, and can be operated in conjunction with the entire system 100. For example, the workstation 103 may communicate with the imaging device 102 so that the image data collected by the imaging device 102 can be rendered at the workstation 103 and viewed on a display device.

The workstation 103 may communicate directly with the computer system 101 to display processed image data and/or output image processing results. The workstation 103 may include a graphical user interface to receive user input via an input device (e.g., keyboard, mouse, touch screen, voice or video recognition interface, etc.) to manipulate visualization and/or processing of the image data. For example, the user may view the processed image data, and specify one or more view adjustments or preferences (e.g., zooming, cropping, panning, rotating, changing contrast, changing color, changing view angle, changing view depth, changing rendering or reconstruction technique, etc.), navigate to a particular region of interest by specifying a "goto" location, navigate (e.g., stop, play, step through, etc.) image volumes, and so forth.

Endoscopic instrument 130 may be inserted into the patient's body to examine the interior of a tubular network (e.g., respiratory tract or airway). One example of an endoscopic instrument 130 is a bronchoscope, which includes an elongated rigid or flexible tube having a light source and a video camera for providing one or more real-time video images to the computer system 101 from the bronchoscope's tip. The bronchoscope may further include a working channel (or sheath) through which one or more instruments (e.g., biopsy or therapeutic catheters) may be inserted. For example, a catheter may be inserted in the working channel to take specimens from inside the lungs for diagnosis or to administer treatment (e.g., radiofrequency, laser or microwave ablation).

An electromagnetic (EM) tracking system 135 may optionally be provided to localize the endoscopic instrument 130 through the use of electromagnetic technology. The EM tracking system 135 may include a steerable guide catheter that contains a position sensor at its distal tip. The steerable guide catheter may be advanced through the working channel of the endoscopic instrument 130. The EM tracking system 135 may provide the tracked three-dimensional (3D) position (e.g., x, y, z coordinates) of its distal tip when moving in the EM field. The 3D position information may be provided to the computer system 101 in real-time. EM tracking system 135 may also communicate with imaging device 102.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2A:
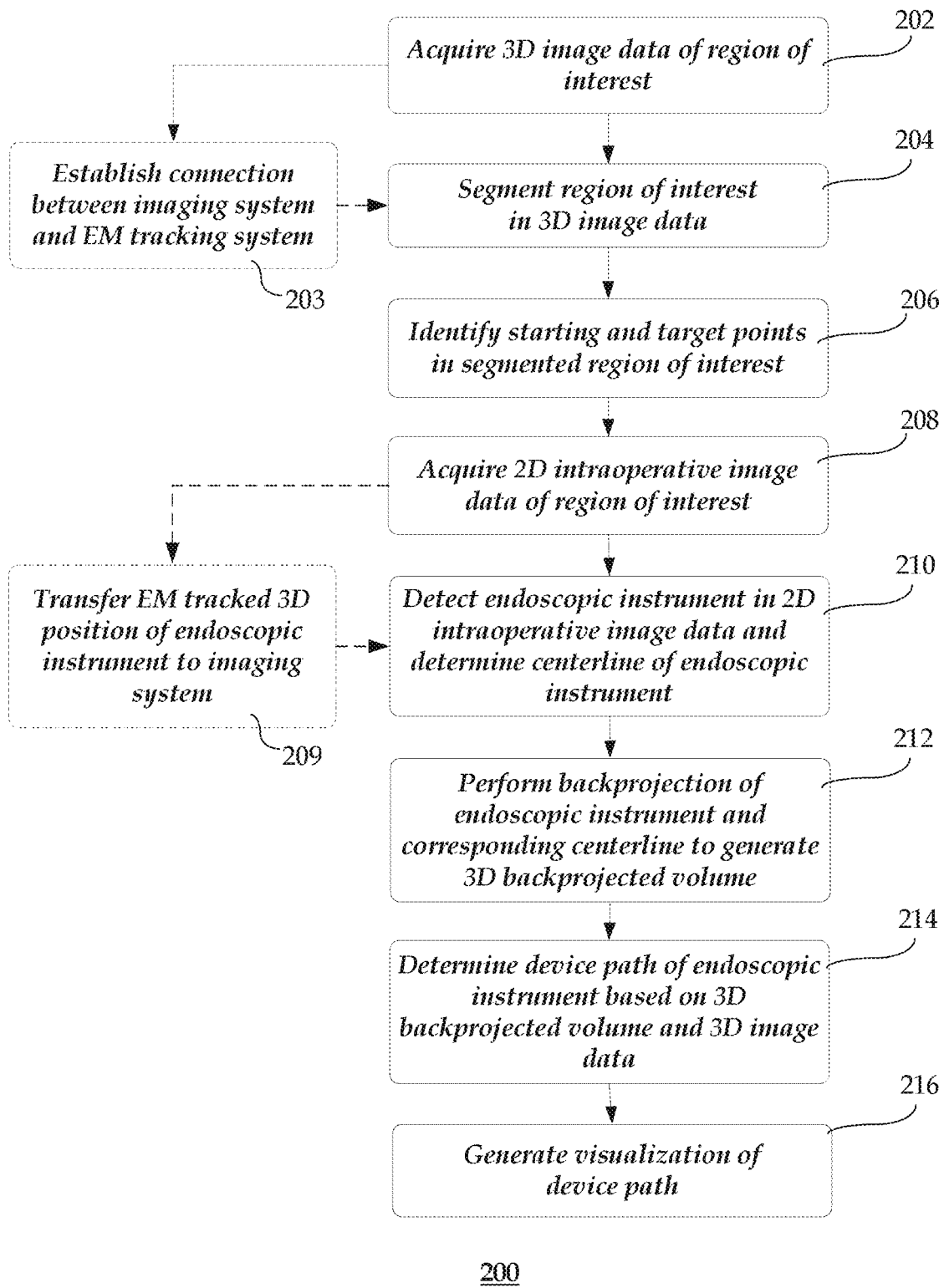
FIG. 2a shows an exemplary method of image-based guidance by a computer system.

FIG. 2a shows an exemplary method 200 of image-based guidance by a computer system. It should be understood that the steps of the method 200 may be performed in the order shown or a different order. Additional, different, or fewer steps may also be provided. Some optional steps are delineated with broken lines. Further, the method 200 may be implemented with the system 100 of FIG. 1, a different system, or a combination thereof At 202, imaging device 102 acquires 3D image data of a region of interest in the patient. Imaging device 102 may be a scanner or C-arm system with a single imaging plane or multiple imaging planes. For example, imaging device 102 may include a rotating CT gantry covering at least one pair of X-ray source and X-ray detector. In other implementations, imaging device 102 is a rotating optical CT gantry covering at least one pair of light source and optical detector. Other types of imaging device 102 may also be used.

Figure 3:
FIG. 3 shows various exemplary views reconstructed from a three-dimensional (3D) computed tomographic (CT) image volume of a lung.

The region of interest may be any region that is identified for study, such as at least a portion of a tubular network (e.g., lungs, airway, bronchial tree). The 3D image data is acquired before (i.e. pre-operatively) or during a medical procedure (i.e. intraoperatively) performed on the patient. The 3D image data may be generated by acquiring tomographic image slices in different directions and combining them into a 3D image volume. FIG. 3 shows various exemplary views 302a-d reconstructed from a 3D CT image volume of a lung. In some implementations, the 3D image data is registered to (or aligned with) the patient. Such image-to-patient registration may be rigid (e.g., landmark-based or centerline-based) or nonrigid (or deformable).

Returning to FIG. 2a, at optional step 203, a connection is established between imaging device 102 and EM tracking system 135. As discussed previously, the EM tracking system 135 may be optionally provided as an additional information source for generating guidance to navigate the endoscopic instrument 130. If the EM tracking system 135 is used, guidance generator 106 may load data into the EM tracking system 135 and establish a connection between the imaging device 102 and the EM tracking system 135. The guidance generator 106 may load, for example, 3D image datasets (e.g., CT scan data of the region of interest) into the EM tracking system 135. The connection between the imaging device 102 and the EM tracking system 135 may be accomplished through a network connection to allow transfer of image and/or position coordinate data.

At 204, guidance generator 106 segments the region of interest in the 3D image data. One method of segmentation uses a threshold (e.g., setting a lower or upper limit) for the Hounsfield unit (HU) of the image data. Pixels with density values in the preset range are carried over to the segmented region of interest. Other methods of segmentation, such as region growing or connected component techniques, are also useful. The centerline of the segmented region of interest may also be detected and represented by a set of points. The segmented region of interest reflects the path that the endoscopic instrument 130 is restricted to follow. Labels may be assigned to identify the branches of the tubular network (e.g., bronchial tree).

At 206, the starting and target points are identified in the segmented region of interest. The starting point is where the tip of the endoscopic instrument 130 is inserted or the position where the navigation starts, while the target point is where the clinician plans to navigate the tip of the endoscopic instrument 130. The starting and target points may be selected by the clinician via, for example, a user interface at workstation 103. For example, the user interface may be generated and presented to the clinician to display a view of the 3D image data with the segmented region of interest and enable the clinician to digitally mark the starting and target points within the segmented region of interest.

Guidance generator 106 may further generate suggestions of optimal views of the segmented region of interest to reduce airway ambiguity during such user selection. The optimal view may be determined by, for example, calculating the viewing angle that provides a view of the segmented region of interest that is orthogonal to the direction of the X-ray beam. Such optimal views may be displayed via the user interface at workstation 103.

At 208, imaging device 102 acquires 2D intraoperative image data of the region of interest. The 2D intraoperative image data may be acquired at one or more specific time points during the medical procedure. When an EM tracking system 135 is used, the 2D intraoperative image data may be acquired at specific time points across, for example, a breathing cycle to generate a sequence of 2D intraoperative images. When the medical procedure is started, an endoscopic instrument 130 may be inserted into a tubular network of the patient. For example, a bronchoscope may be inserted through the patient's nose, mouth or a tracheostomy, and advanced through the bronchial (or airway) tree. A catheter may be inserted into the working channel of the bronchoscope to, for example, administer treatment or perform a biopsy for diagnostic purposes.

Figure 4:
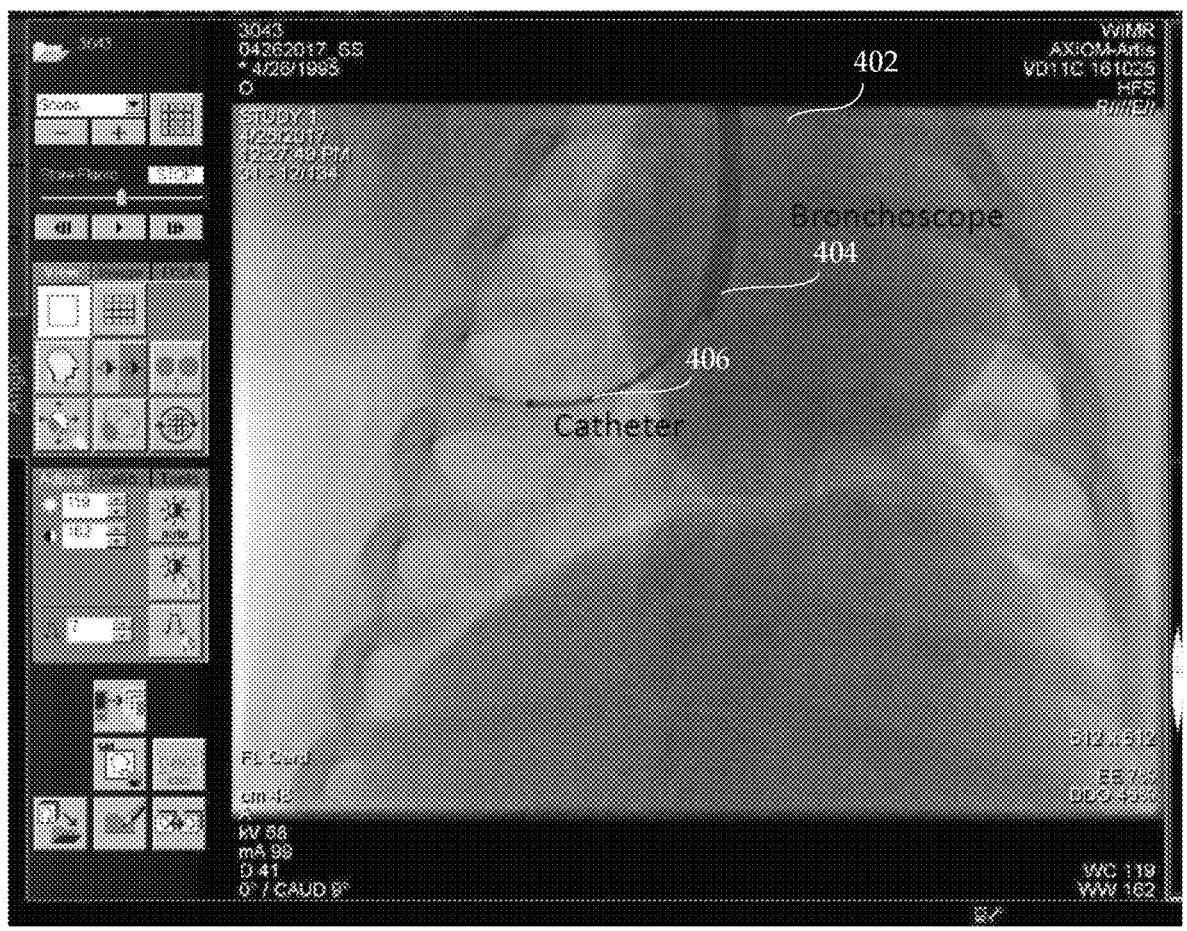
FIG. 4 shows an exemplary two-dimensional (2D) fluoroscopic image of a patient's lungs.

The 2D intraoperative image data may include, for example, one or more 2D fluoroscopic images. FIG. 4 shows an exemplary 2D fluoroscopic image 402 of a patient's lungs. The 2D fluoroscopic image 402 shows a bronchoscope 404 inserted into a bronchial network during an ablation procedure. A catheter 406 is inserted into the working channel of the bronchoscope 404 and extends beyond the tip of the bronchoscope 404 to administer ablation for treatment of lung cancer.

Returning to FIG. 2a, at optional step 209, when an EM tracking system 135 is used, the EM tracked 3D position (e.g., x, y, z coordinates) of the distal tip of the endoscopic instrument 130 is acquired with each 2D intraoperative image at each time point and translated into the coordinate system of the imaging system 102. In some implementations, information from the EM tracking system 135 in the form of, for example, 3D CT scan image data and the position of the tip of the EM tracked endoscopic instrument in this image data, is sent to the imaging system 102. Such information may be fused with, for example, a cone beam computed tomography (CBCT) image acquired at the beginning of the medical procedure. Alternatively, a 3D to 2D fusion of the CT image with the fluoroscopy images may be performed around the time of data transfer. The translated 3D position information may then be communicated to the imaging device 102 and/or computer system 101.

At 210, guidance generator 106 detects an endoscopic instrument 130 in the 2D intraoperative image data and determines the centerline of the endoscopic instrument 130. As discussed previously, the endoscopic instrument 130 may be, for example, a bronchoscope with a catheter and optionally an EM steerable guide catheter with a position sensor inserted into its working channel. The endoscopic instrument 130 may be detected using a region detection algorithm or any other suitable image analysis algorithm. The centerline may be calculated and represented by a locus of points that form the center path defining the approximate centerline of the endoscopic instrument 130 and any catheter extending beyond the tip of the endoscopic instrument 130.

Figure 5:
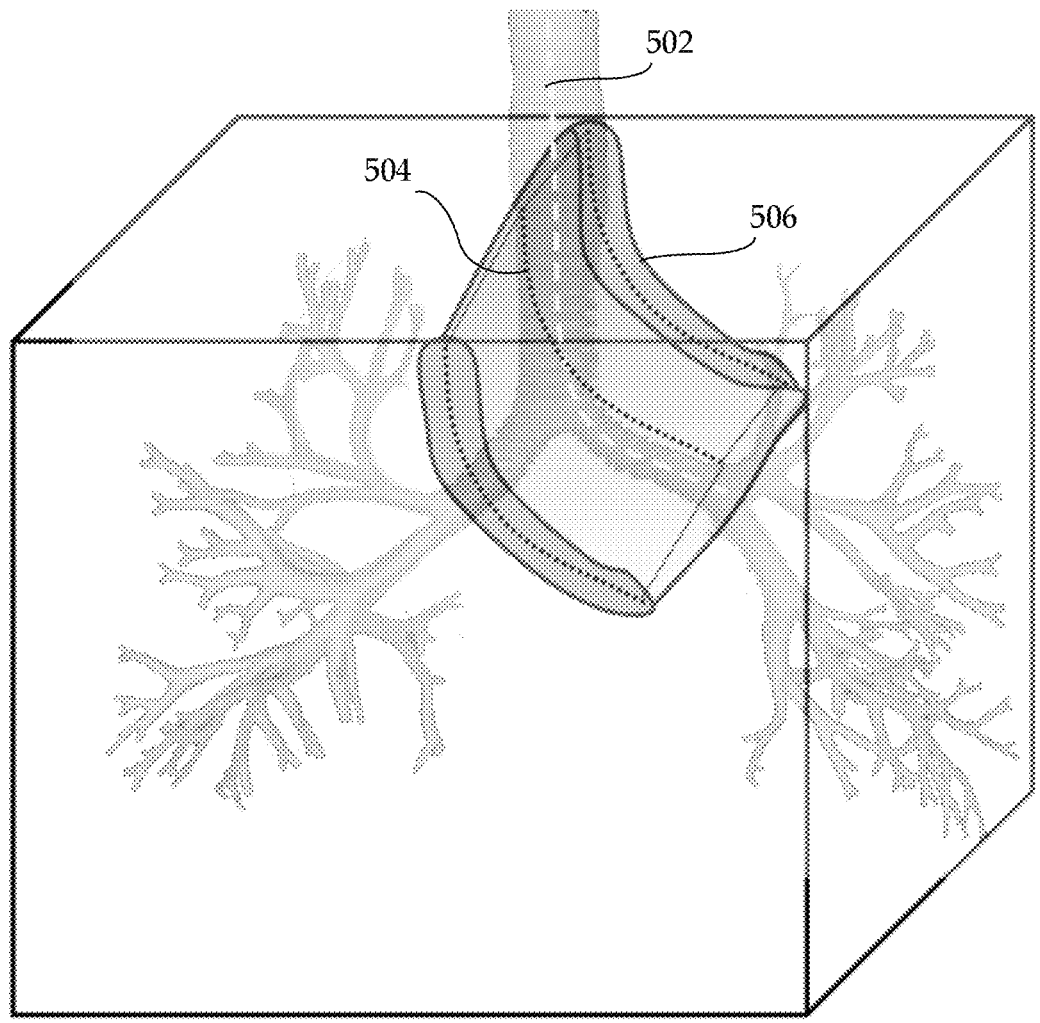
FIG. 5 illustrates an exemplary backprojection of the detected bronchoscope and its corresponding centerline.

At 212, guidance generator 106 performs backprojection of the detected endoscopic instrument 130 and corresponding centerline to generate a three-dimensional (3D) backprojected volume. In some implementations, backprojection may be performed for each 2D image in a sequence of intraoperative images captured across different time points to generate a set of 3D backprojected volumes. Angiographic systems may be calibrated to enable 3D reconstruction (e.g., single view 3D reconstruction). FIG. 5 illustrates an exemplary backprojection of the detected bronchoscope and its corresponding centerline. The centerline 502 of a bronchus is shown. The edges and centerline 504 of the detected bronchoscope are backprojected to form a 3D volume 506. The backprojection may be performed using known system geometry.

Referring back to FIG. 2a, at 214, guidance generator 106 determines the device path of the endoscopic instrument 130 based at least in part on the 3D backprojected volume and the 3D image data. The device path is the most likely or correct passage of the tip of the endoscopic instrument 130 from the starting point to the target point (or most distal segment) in the region of interest.

Figure 2B:
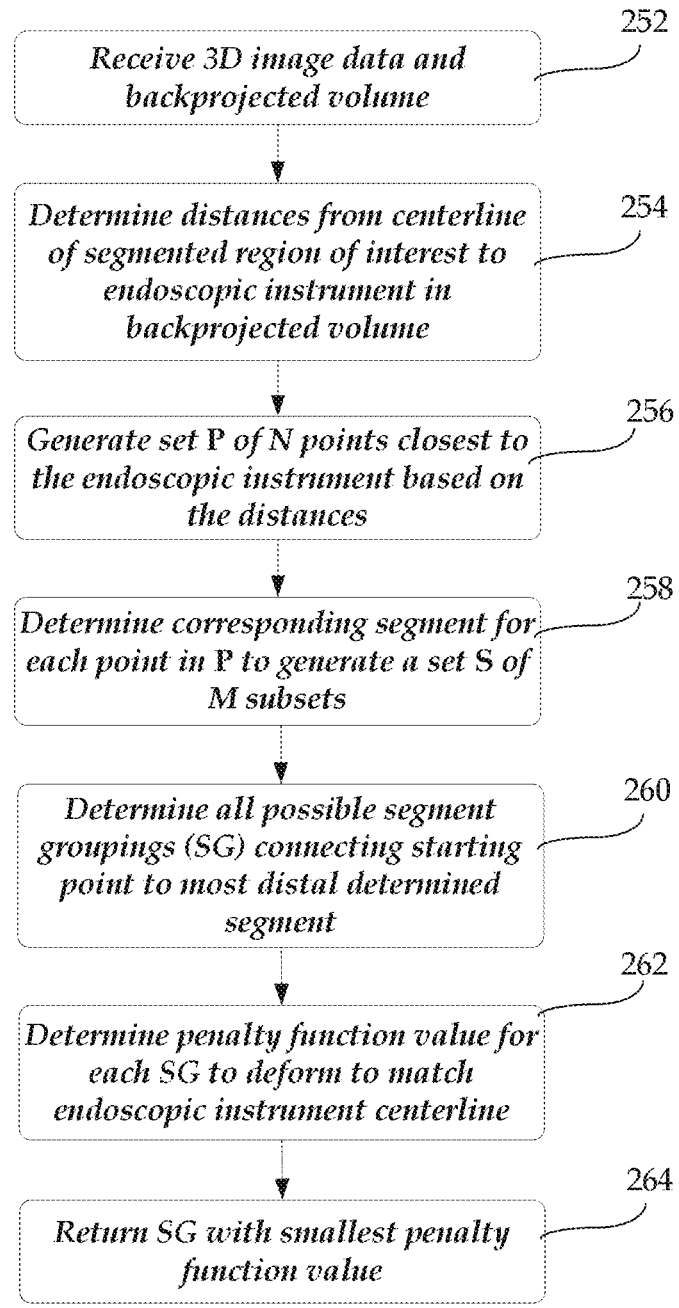
FIG. 2b shows an exemplary method of determining a device path.

FIG. 2b shows an exemplary method 214a of determining the device path. It should be understood that the steps of the method 214a may be performed in the order shown or a different order. Additional, different, or fewer steps may also be provided. Further, the method 214a may be implemented with the system 100 of FIG. 1, a different system, or a combination thereof.

At 252, guidance generator 106 receives the 3D image data and the backprojected volume. As discussed previously, the 3D image data may be acquired pre-operatively or intraoperatively by imaging device 102. The 3D image data may include the segmented region of interest and its corresponding centerline, as well as the starting and target points of the endoscopic instrument 130. The backprojected volume may be derived from the 2D intraoperative image data of the region of interest and may include the 3D backprojected endoscopic instrument 130 and its corresponding centerline.

At 254, guidance generator 106 determines distances from the centerline of each segment S of the segmented region of interest to the centerline of the endoscopic instrument 130 in the backprojected volume. More particularly, the shortest distance from each point along the centerline of the segmented region of interest to the backprojected centerline of the endoscopic instrument 130 is determined, resulting in N data points or distances for each segment S. The segment S may be, for example, a segment of a bronchial network or any other tubular network.

Figure 6:
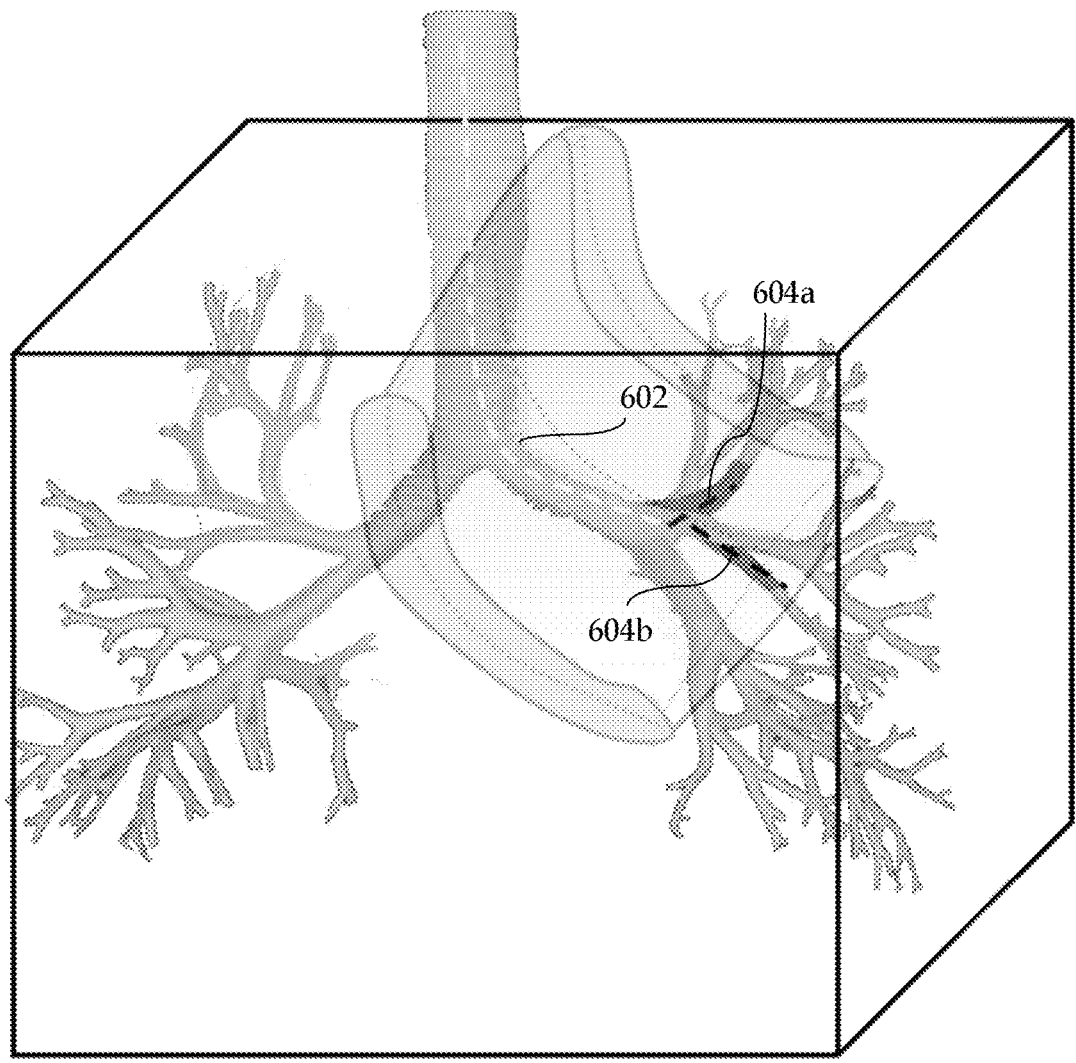
FIG. 6 shows exemplary candidate segments.

At 260, guidance generator 106 determines all possible segment groupings (SG) from the set of segments S. Each SG is a set of one or more segments that directionally connect the main segment of the tubular network (i.e., where the starting point resides) to the determined segment that is most distal to the starting point (i.e., where the target point resides). All possible segment groupings satisfying directional continuity may be considered. FIG. 6 shows exemplary candidate segments 604a-b. Candidate segments 604a-b connect to the main bronchus 602 of the bronchial network.

At 262, guidance generator 106 determines the penalty function value for each segment grouping SG to the backprojected centerline of the endoscopic instrument based at least in part on the N shortest distances. The penalty function value may be calculated by determining a normalized sum of the shortest distances ($P_i$) of points along a centerline in a given segment grouping SG to the backprojected centerline of the endoscopic instrument and the deformation to be applied to the segment grouping SG to contain the endoscopic instrument. The combined weighted sum of these calculations is called a penalty function. An exemplary penalty function F is provided as follows:

$$F = w_1(\text{Sum}(P_i)/\text{Length}(SG)) + w_2\text{Mag}(D) \qquad (1)$$

wherein D is the deformation field needed to create an intersection between the segmented region of interest and the plane created by backprojecting the endoscopic instrument; Mag(D) is the magnitude of the deformation field D; $w_1$ and $w_2$ are predetermined weights; Sum($P_i$) is the sum of shortest distances ($P_i$) of all points i along a centerline of a given segment SG to the backprojected centerline of the endoscopic instrument, wherein i=1 to N; and Length(SG) is the length of the given segment grouping SG. It should be noted that the larger the tubular segment, the more difficult it is to deform and an additional penalty weight may be introduced into the deformation field to represent this.

At 264, guidance generator 106 selects and returns the segment grouping with the smallest penalty function value. This segment grouping forms at least a portion of the device path of the endoscopic instrument and may be presented to the user in, for example, a visualization.

Figure 2C:
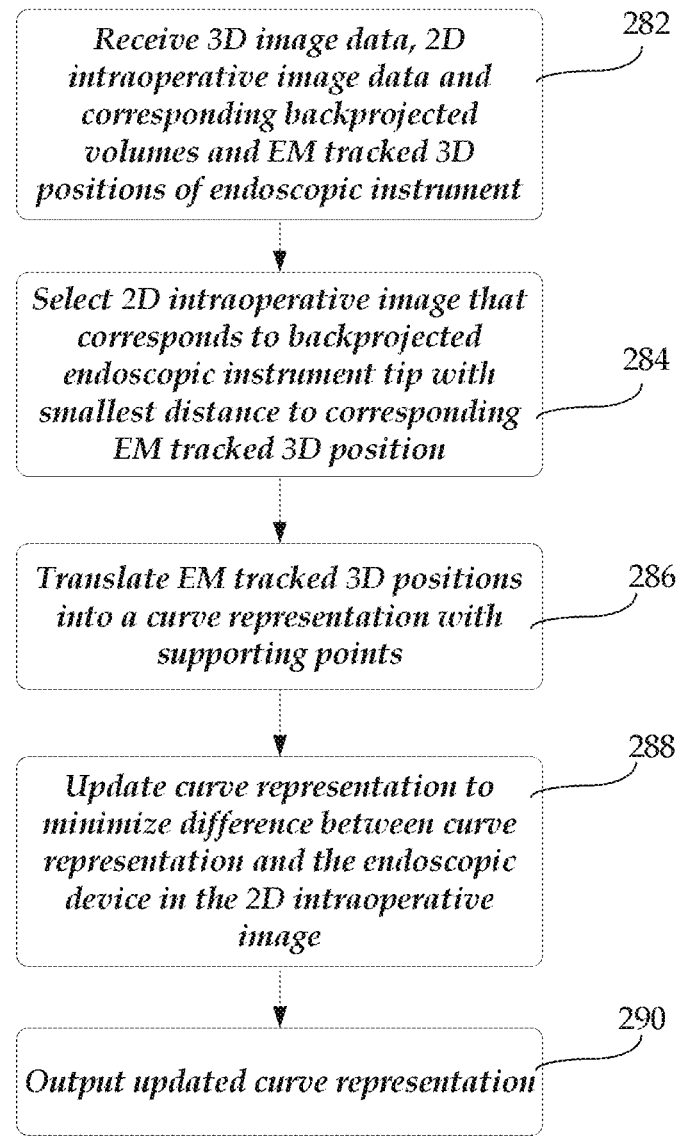
FIG. 2c shows another exemplary method of determining a device path.

FIG. 2c shows another exemplary method of determining the device path. It should be understood that the steps of the method 214b may be performed in the order shown or a different order. Additional, different, or fewer steps may also be provided. Further, the method 214b may be implemented with the system 100 of FIG. 1, a different system, or a combination thereof At 282, guidance generator 106 receives the 3D image data of the region of interest, 2D intraoperative image data of the region of interest and corresponding backprojected volumes and EM tracked 3D positions of the endoscopic instrument 130. As discussed previously, the 3D image data may be acquired pre-operatively or intraoperatively by imaging device 102. The 3D image data may include the segmented region of interest and its corresponding centerline, as well as the starting and target points of the endoscopic instrument 130.

The backprojected volumes may be derived from a sequence of 2D intraoperative image data of the region of interest acquired at different time points. For example, the sequence of 2D intraoperative image data may be fluoroscopic images acquired during a breathing cycle with the endoscopic instrument 130 in the bronchus not moving. Each backprojected volume may include the 3D backprojected endoscopic instrument 130 and its corresponding centerline. Additionally, EM tracked 3D positions (e.g., x, y, z coordinates) of the distal tip and support points along the flexible shaft of the endoscopic instrument 130 may also be received. The EM tracked 3D positions may correspond to the sequence of intraoperative 2D image data acquired at different time points.

At 284, guidance generator 106 selects the intraoperative 2D image E from the sequence of intraoperative 2D image data that corresponds to a backprojected endoscopic instrument tip that has the smallest distance to its corresponding EM tracked 3D position.

At 286, guidance generator 106 translates the EM tracked 3D positions of the endoscopic instrument tip into a curve representation C with supporting points. The curve representation may be, for example, a B-spline (or basis spline). A B-spline function is a combination of flexible bands that passes through a number of supporting points and creates smooth curves.

At 288, guidance generator 106 updates the curve representation C to minimize the difference between the curve representation C and the backprojected plane of endoscopic instrument derived from the selected intraoperative 2D image E. This may be performed by modifying the supporting points of the curve representation C to satisfy an objective function that takes into account the overall tortuosity of the endoscopic instrument, the translation of each supporting point as well as the stiffness of the tubular segment (e.g., the larger an airway diameter, the stiffer it is). An exemplary objective function is provided as follows:

$$\text{argmin}(w_1(C \cap E) + w_2 T(C) + w_3 \text{Mag}(D)) \qquad (2)$$

wherein T() is a function that calculates the bending energy contained in C; D is the deformation field needed to create an intersection between the segmented region of interest and the plane created by backprojecting the endoscopic instrument; Mag(D) is the magnitude of the deformation field D; and $w_1$, $w_2$ and $w_3$ are predetermined weights. Supporting points of the curve representation C may be updated by defining directions for each supporting point that minimizes the objective function, moving a small amount in those directions. The 3D tubular network model may then be deformed to include the updated curve representation C.

At 290, guidance generator 106 outputs the updated curve representation. Such updated curve representation may be used to form at least a portion of the device path of the endoscopic instrument that is presented to the user. The updated curve representation and induced changes in the 3D tubular network model may further be transferred to the EM tracking system 135, so as to improve overall EM tracking accuracy.

The method 214b may be repeated as necessary. Once the endoscopic instrument 130 is moved out of the tubular network, this approach works similarly, but the constraint of the tubular network in the objective function may be dropped.

Figure 7:
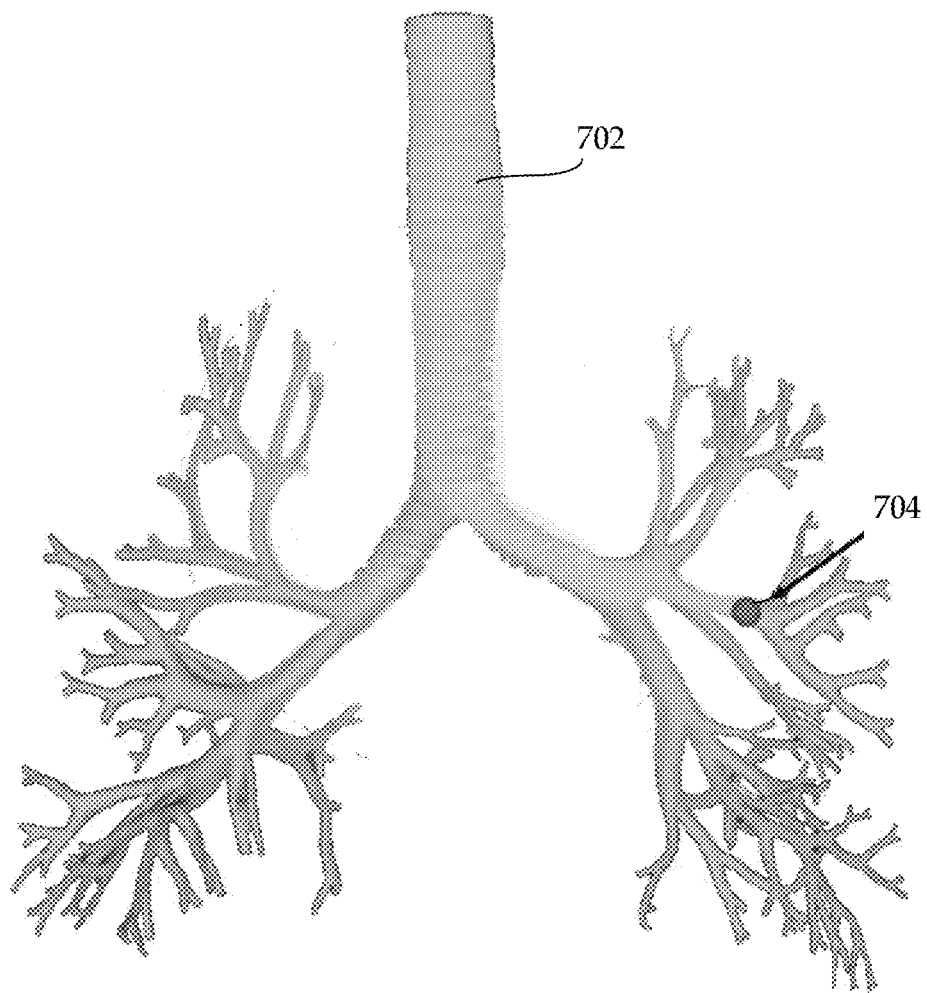
FIG. 7 shows an exemplary visualization.

Referring back to FIG. 2a, at 216, visualization unit 107 generates a visualization of the device path of the endoscopic instrument 130. The visualization may highlight (e.g., in different color or shading) the device path on image data of the region of interest. FIG. 7 shows an exemplary visualization. The device path 702 is highlighted in the image data. The most distal point 704 of the device path is visualized as the determined tip of the endoscopic instrument in a 3D viewing mode with respect to the desired target position.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. An image-based guidance method, comprising:
   segmenting, by a processor, a region of interest in three-dimensional (3D) image data to generate a segmented region of interest;
   detecting, by the processor, a region of an endoscopic instrument in two-dimensional (2D) intraoperative image data of the region of interest and determining a centerline of the detected region of the endoscopic instrument;
   performing, by the processor, backprojection of the endoscopic instrument and the centerline to generate a 3D backprojected volume including the backprojected endoscopic instrument and the backprojected centerline;
   determining, by the processor, a device path of the endoscopic instrument based at least in part on distances from a centerline of the segmented region of interest to the backprojected centerline of the backprojected endoscopic instrument,
   wherein determining, by the processor, the device path of the endoscopic instrument based at least in part on the distances from the centerline of the segmented region of interest to the backprojected centerline of the backprojected endoscopic instrument comprises:
   determining one or more segment groupings, wherein each of the one or more segment groupings comprises a set of one or more segments that directionally connect a main segment of the segmented region of interest to a most distal segment of the segmented region of interest;
   determining one or more penalty function values for the one or more segment groupings, wherein the one or more penalty function values are based on shortest distances between a centerline of a segment of the segmented region of interest and the backprojected centerline; and
   selecting at least one of the one or more segment groupings with a smallest penalty function value, wherein the selected segment grouping forms at least a portion of the device path; and
   generating, by the processor, a visualization of the device path from a starting point to a target point.

2. The method of claim 1 further comprises acquiring the 3D image data of the region of interest, wherein the region of interest comprises at least a portion of a bronchial tree.

3. The method of claim 1 further comprises acquiring the 2D intraoperative image data of the region of interest during a medical procedure.

4. The method of claim 3 wherein acquiring the 2D intraoperative image data comprises acquiring one or more 2D fluoroscopic images.

5. The method of claim 1 further comprises determining a centerline of the segmented region of interest.

6. The method of claim 1 further comprises identifying, via a user interface, the starting point and the target point of the endoscopic instrument in the segmented region of interest.

7. The method of claim 1 wherein determining the one or more penalty function values comprises determining a normalized sum of the shortest distances.

8. The method of claim 7 wherein determining the one or more penalty function values further comprises calculating a magnitude of a deformation field to be applied to the one or more segment groupings to contain the endoscopic instrument.

9. The method of claim 1 further comprises acquiring electromagnetic (EM) tracked 3D positions of a tip of the endoscopic instrument corresponding to a sequence of the intraoperative 2D image data at different time points.

10. The method of claim 9 wherein determining, by the processor, the device path of the endoscopic instrument based at least in part on the distances from the centerline of the segmented region of interest to the backprojected centerline of the backprojected endoscopic instrument comprises:
    selecting an image from the sequence of the intraoperative 2D image data that corresponds to a backprojected endoscopic instrument tip with a smallest distance to a corresponding EM tracked 3D position;
    translating the EM tracked 3D positions into a curve representation; and
    updating the curve representation to minimize a difference between the curve representation and a backprojected plane of the endoscopic instrument derived from the selected image, wherein the updated curve representation forms at least a portion of the device path.

11. The method of claim 10 wherein translating the EM tracked 3D positions into the curve representation comprises translating the EM tracked 3D positions into a basis spline.

12. The method of claim 10 wherein updating the curve representation comprises modifying supporting points of the curve representation to satisfy an objective function.

* * * * *